United States Patent [19]

Crahay et al.

[11] Patent Number: 5,124,256
[45] Date of Patent: Jun. 23, 1992

[54] PROCESS FOR RECOVERING POLYPEPTIDES LOCALIZED IN THE PERIPLASMIC SPACE OF YEAST WITHOUT BREAKING THE CELL WALL BY USING AN NON-IONIC DETERGENT AND A NEUTRAL SALT

[75] Inventors: Jacques Crahay, Mazy; Jean M. A. G. Delcour, Walhain; Jacques D. V. Hanotier, Lasne, all of Belgium

[73] Assignee: Labofina, S.A., Feluy, Belgium

[21] Appl. No.: 607,844

[22] Filed: Nov. 5, 1990

Related U.S. Application Data

[63] Continuation of Ser. No. 929,436, Nov. 12, 1986, abandoned.

[30] Foreign Application Priority Data

Nov. 13, 1985 [BE] Belgium .................................. 903626

[51] Int. Cl.$^5$ .................... C12P 21/00; C12N 9/00; C12N 9/36; C07K 3/02
[52] U.S. Cl. .................................. 435/71.1; 435/183; 435/206; 530/424
[58] Field of Search .................. 435/206, 183, 71.1; 530/422, 424, 824

[56] References Cited

U.S. PATENT DOCUMENTS

| | | | |
|---|---|---|---|
| 3,917,510 | 11/1975 | Kitamura | 435/259 |
| 4,683,293 | 7/1987 | Craig | 530/359 |
| 4,683,294 | 7/1987 | Van Wijnendaele | 530/371 |

OTHER PUBLICATIONS

Muraki, M. et al., *Agric. Biol. Chem.*, 49(a): 2829-2831 (Sep. 1985).
Teich et al., *Chem. Abstracts* 92(3): 196398c, p. 518 (1980).
Yasudo et al. *Chem. Abstracts* 91(1):3933w, (1979).
Tuite et al. *EMBO J.* 1(5): 603-608 (1982).
Scopes, *Protein Purification*, Springer-Verlag, New York, © 1982, pp. 36 and 37.
Hitzeman et al.; *Nucleic Acids Research*, 11(9):2745-2763, (1983).
Ota, Y et al., Agric. Biol. Chem 46(12):2885-2893 (82) Purification and some Properties of Cell-Bound Lipase.
Schwencke et al., Eur. J. Biochem 21:137-143 (71) The Release of Extracellular Enzymes from Yeast by "Osmotic Shock".
G. L. Stetler et al. BIO/TECHNOLOGY, vol. 7, pp. 55 to 60, Jan. 1989 "Secretion of Active, Full-and Half-Length Human Secretory Leukocyte Protease Inhibitor by *Saccharomyces Cerevisiae*".

*Primary Examiner*—Douglas W. Robinson
*Assistant Examiner*—S. Saucier
*Attorney, Agent, or Firm*—Roger W. Parkhurst; John K. Abokhair; M. Norwood Cheairs

[57] ABSTRACT

The invention relates to a process for releasing into aqueous medium polypeptides produced by yeasts and localized at least partially within the periplasmic space thereof without breaking the yeast cell. The process involves treating the yeasts in aqueous medium with a neutral water-soluble mineral salt and a non-ionic water-soluble polyethoxylated alkylphenol surfactant having an HLB of between 8 and 15.

9 Claims, No Drawings

PROCESS FOR RECOVERING POLYPEPTIDES LOCALIZED IN THE PERIPLASMIC SPACE OF YEAST WITHOUT BREAKING THE CELL WALL BY USING AN NON-IONIC DETERGENT AND A NEUTRAL SALT

This is a continuation of application Ser. No. 06/929,436 filed Nov. 12, 1986, now abandoned.

BACKGROUND OF THE INVENTION

1. Field of the Invention

The present invention relates to a process for releasing into aqueous medium polypeptides produced by yeasts and localized at least partially in the periplasmic space thereof. More particulary, it relates to a process for releasing into aqueous medium the lysozyme produced by yeasts genetically engineered for that purpose.

2. Description of the Art

The yeast *Saccharomyces cerevisiae* is increasingly used as a host for genetic manipulations aimed at producing polypeptides of commercial interest by fermentation. The increasing use of yeast is attributable to the various advantages that it shows over other industrial microorganisms, e.g., the fact that yeast is above all an alimentary organism. Another advantage of yeast is that its culture does not require absolute sterile conditions, so that it is particulary appropriate for large scale fermentations. In addition, its ability to live under anaerobic conditions makes it suitable in immobilized form for the continuous production of metabolites.

When using yeast for producing polypeptides, e.g., enzymes, it obviously is important that these be secreted through the plasmic membrane and excreted into the fermentation medium, from which they can then be recovered by using well known techniques such as adsorption or affinity chromatography. It is known that proteins secreted through the plasmic membrane of yeast tend to remain confined to the periplasmic space or at least to remain associated with the cell wall. This is often observed in yeasts of the Saccharomyces genus and particularly in the *S. cerevisiae* species (see R. SCHEKMAN and P. NOVICK, "The Molecular Biology of Yeast Saccharomyces, Metabolism and Gene Expression", J. N. Strathern et al. Eds, Cold Spring Harbor, N.Y., 1982, pp. 361-393). This peculiarity which may bring some functional advantage to yeast is, however, a major disadvantage from a practical standpoint when the production of proteins of commercial interest by fermentation is to be carried out. Indeed, in such a case, the benefit brought by secretion for recovering the protein of interest is lost since said protein, by remaining associated with the cells, must be separated from the whole of the cellular materials as in the case of an intracellular protein. This tendency of yeast to keep the proteins they secrete associated with their wall has been attributed to the fact that most of these proteins are heavily glycosylated. This is the case for invertase and for acid phosphatase which both contain a large proportion of polysaccharides comprising essentially mannose. One function of the glycosylated portion of these proteins would be to maintain their association with the polysaccharide matrix of the walls comprising essentially itself mannose (see J. O. LAMPEN, Antonie van Leeuwenhoek, 34, 1-18, 1968). According to this interpretation, the excretion into the medium of the α factor of Matα-type yeasts or of the "killer" protein produced by some yeast strains can be explained by the fact that they are not glycosylated.

However, when non-glycosylated heterologous proteins are expressed in yeast, frequently only a fraction of the protein formed is excreted into the medium, even when it is equipped with a signal sequence allowing its secretion through the plasmic membrane. This is the case for human αlinterferon (see A. SINGH et al., Nucleic Acids Res., 12, 8927-8938, 1984) the secretion of which was ensured by fusion of the corresponding gene with the DNA coding for the leader sequence of the precursor of the yeast α factor: only one-half thereof is found in the medium. This is also the case for chicken lyzozyme secreted due to its own signal sequence (see Belgian Patent No. 901,223). In such cases, it obviously is possible to recover only the soluble fraction of the protein but this would result in a loss of yield.

It also is possible to recover the fraction remaining associated with the cell, but this would require additional operations. Either solution would result in increased production costs which will reduce to some extent the above-enumerated advantages of utilizing yeast as a production organism.

SUMMARY OF THE INVENTION

The main object of the present invention is to provide a process to facilitate recovery in a high yield the polypeptides produced and secreted by yeast but which remain partially or totally localized within the periplasmic space. More specifically, the object of the present invention is to recover in high yield the heterologous proteins produced and excreted at least partially into a medium by yeasts which are genetically engineered for that purpose. Still more specifically, the object of the present invention is to recover from the yeast *S. cerevisiae* the lysozyme produced therein and selected as a result of a genetic manipulation.

According to the present invention, these objects are achieved by a process comprising treating an aqueous medium of yeasts with a neutral water-soluble mineral salt and a water-soluble non-ionic polyethoxylated alkylphenol surfactant with an HLB (Hydrophilic Lipophilic Balance) of between 8 and 15.

DETAILED DESCRIPTION OF THE INVENTION

It is known that the presence of sufficient concentrations of sodium chloride or of other salts such as KCl or $NaNO_3$ in the culture medium of yeast favors the liberation therein of soluble proteins. Thus, it was shown that in the presence of 0.6M NaCl the amount of proteins in the medium after 6 hours culture of a bakers' yeast in an aerated medium was three times higher than in the absence of salt (T. A. FRANKLIN et al., Biotechnology and Bioengineering Symp. No. 14, 467, 1984). This result cannot be explained by a liberation of proteins as a result of an osmotic shock, as it is admitted that the periplasmic proteins of *S. cerevisiae* are not liberated by this treatment (see W. N. ARNOLD, Physical Aspects of the Yeast Cell Envelope; in Yeast Cell Envelopes: Biochemistry, Biophysics and Ultrastructure vol. 1, Ed. W. N. ARNOLD, CRC Press Inc., Boca Raton, Fla., 1981, p. 25-47). Although the mechanism of action of the salt is not precisely known, it is assumed that ionic bonds may be present between the yeast cell wall and proteins soluble in the medium, the effect of the salt being to break these bonds and to liberate the proteins.

This phenomenon can also be evidenced by the following experiment.

Yeasts (*S. cerevisiae*, GRF18 strain) grown in a minimal medium (3% glucose, 0.67% yeast nitrogen base, 0.002% histidine and leucine) and harvested at the beginning of the stationary phase are resuspended in a 0.1M phosphate buffer with a pH of 6.5 to which chicken lysozyme (Boehringer Ingelheim) was added up to a concentration of 670 units/ml suspension. After 2 hours of incubation at 37° C., the cells are separated by centrifugation and the lysozyme present in the supernatant is determined by the method of D. SHUGAR (see Biochem. Biophys. Acta 8, 302–309, 1952). The lysozyme concentration is only 440 units/ml (i.e., 66% of the initial value). The same result is observed at 0° C. This cannot be attributed to a partial deactivation of the enzyme during incubation, because lysozyme incubated at the same concentration and at the same temperatures in the supernatant of the initial culture does not show any loss of activity.

In another experiment, after one hour of incubation at 4° C. in the presence of lysozyme, NaCl was added up to a concentration of 0.5M to the yeast suspension which was further incubated at 30° C. for 2 hours. The suspension was then centrifugated and the lysozyme present in the supernatant was determined as described above. It was determined that 98% of the initial lysozyme is in solution in the supernatant, as opposed to 38% when NaCl is omitted in another identical experiment.

These experiments tend to show that extraneous lysozyme binds reversibly to the yeast cell wall, wherefrom it can be released quantitatively by increasing the ionic strength of the medium. The situation is not the same when lysozyme associated with the cells results from the expression therein of a cloned gene. It is known from Belgian Patent No. 901,223 that it is possible to clone and express in yeast foreign genes coding for enzymes having a 1,4-β-N-acetylmuramidasic activity, e.g., the gene coding for chicken lysozyme. The lysozyme thus formed in yeast shows such an activity; it is partially present in the culture medium, from which it was separated by adsorption on fast flow carboxymethylsepharose (Pharmacia) in a 0.1M phosphate buffer with a pH of 6.5, followed by washing with the same buffer then by elution in the same buffer supplemented with 0.5M NaCl. The eluate was then concentrated by ultrafiltration, desalted by passage over Sephadex G-25 (Pharmacia), reconcentrated by ultrafiltration and dried by lyophilisation. Electrophoresis on polyacrylamide gel in the presence of sodium dodecylsulfate showed only one protein band, with an electrophoretic mobility identical to that of commercial chicken lysozyme extracted from egg white. As a matter of fact, the sequence of the first ten amino acids of the N-terminal end of the protein extracted from the culture medium by the hereinabove described method was shown to be identical to that of mature chicken lysozyme. This result clearly demonstrates that the signal peptide of the prelysozyme formed in the yeast by expression of the cloned gene is correctly recognized and processed by the yeast, so that lysozyme is secreted by the yeast in active form. However, as will be evidenced by the following examples, a fraction of the lysozyme produced by the yeast is not liberated in the medium even when, as suggested by the hereinabove described experiment, the cells are incubated in the presence of 0.5M NaCl. This lysozyme fraction can be detected after grinding the cells and centrifuging the cell debris, especially when grinding is carried out in the presence of 0.5M NaCl. Therefore, the lysozyme corresponds to a soluble fraction (intracellular or periplasmic), even if, as the effect of NaCl seems to indicate, it can partially be absorbed on one or more cell constituents.

However, the possibility exists that a non-negligible portion of the lysozyme produced by the yeast is associated with membrane structures (i.e., plasmic membrane and/or intracellular structures), possibly in the form of prelysozyme. It is known, for example, that calf chymosine expressed in yeast remains for a good part associated with centrifugable cell debris after lysis of the cells, even after a thorough washing thereof (see J. MELLOR et al., Gene 24, 1–14, 1983). In some cases, the proteins associated with membrane structures can be dissolved by treatment with a mild surfactant of the ethoxylated alkylphenol type (see A. HELENIUS and K. SIMONS, Biochem. and Biophys. Acta, 415, 29–79, 1975). This treatment sometimes allows release of the proteins associated with the cells. Thus, by treating a suspension of *Saccharomycopsis lipolytica* with an ethoxylated nonylphenol (Emulgen 950, Kao Atlans Co.), the lipase associated therewith can be dissolved without lysis of the cells (see Y. OTA et al., Agric. Biol. Chem., 46, 2885–2893, 1982). However, when the same procedure is applied to *S. cerevisiae* genetically manipulated to produce lysozyme, no such release can be observed. Even when the yeast cells producing lysozyme are ground in the presence of a polyethoxylated octylphenol such as Triton X-100 (Rohm and Haas) at a concentration of 0.05%, the lysozyme activity determined in the supernatant is not significantly different from that observed in the absence of the surfactant.

These various results show that, in order to recover the major part of the lysozyme produced by yeasts genetically manipulated for that purpose, it is not sufficient to treat the cells with a soluble salt, nor even with a surfactant as suggested by the art. It is still necessary, when resorting to known methods, to destroy the cell structure, thus encountering all the attendant difficulties associated with this operation. It is surprising, therefore, that by treating the cells according to the process of the invention, (i.e., simultaneously treating the cells with a neutral water-soluble salt and with a non-ionic water-soluble surfactant whose hydrophobic moiety comprises a substituted aromatic nucleus) the major part of the lysozyme associated with said cells is recovered, without having to destroy their structure. This shows that a major part of the lysozyme remaining associated with the yeast cells is not of an intracellular nature, but that it is secreted into the periplasmic space thereof.

The salt to be used according to the invention is a water-soluble, neutral mineral salt. Examples of such salts are NaCl, KCl, NaNO$_3$, KNO$_3$, Na$_2$SO$_4$, etc. For both economical and biological reasons, NaCl is preferable. The concentration at which the salt should be used is not critical; a concentration of at least 0.1M will be used in order to obtain desired results. In most cases, there is no advantage to using concentrations higher than 0.5M.

The surfactant to be used according to the invention is non-ionic. In contrast to anionic or cationic surfactants, non-ionic surfactants generally have the essential advantage of not inducing in proteins any conformational modifications which may cause a reduction or even a loss of their biological activity. Applicants have discovered that non-ionic polyethoxylated alkylphenol surfactants produce synergistic effects with water-soluble neutral mineral salts for the recovery of periplasmic proteins. These polyethoxylated alkylphenols are soluble in water and have an HLB between 8 and 15. As typical examples of such agents, there may be cited the polyethoxylated octyl-, nonyl- and tributylphenols, particularly those commercially available under the trademarks Triton X-100, Nonidet P-40, Lutensol AP 8, Synperonic NP 10, Cemulsol OP 9, Sapogenat T-080, etc.

When selecting such a surfactant, it must be taken into account that the activity thereof is influenced not only by the substituted aromatic nucleus but also by the length of the ethoxylated chain. As a general rule, the surfactants selected with an ethoxylated chain length will have an HLB between 8 and 15. When the HLB is lower than 8 the solubility of the surfactant in water is generally insufficient. On the other hand, when the HLB is higher than 15 the synergistic effects associated with the invention are too weak to be of any practical use. The concentration at which the surfactant is to be used also is not very critical. In most cases, a concentration of between 0.02 and 1% will be advantageous.

According to this invention, the yeast cells and polypeptides associated therewith are suspended in an aqueous medium comprising both the soluble neutral salt and the non-ionic surfactant. The operating temperature is not critical. However, in order to minimize the denaturation of the polypeptides to be recovered, operating above room temperature should be avoided. Moreover, it is necessary to allow a sufficient contact time between the cells and the medium. As a general rule, at temperatures close to room temperature, a contact time of between 30 and 120 minutes, more particularly between 45 and 90 minutes, is sufficient to obtain the desired results. The cells are then separated by centrifugation or by any other appropriate technique. The cells then are preferably washed by resuspending them in the same medium or in any other aqueous medium, and ultimately in pure water. They can thereafter be separated again, then pressed or dried, i.e., undergo any useful operation for ensuring their usefulness and value (e.g., as a protein source in animal feeding).

Additionally, the proteins from the medium can be concentrated, separated and purified by any appropriate combination of techniques known in the art (e.g., lyophilisation, ultrafiltration, precipitation, chromatography, etc). The present invention is particularly useful to isolate a protein whose physiochemical properties are such that it is difficult to separate it from a mixture with other proteins. Indeed, a protein which is associated either totally or partially with the periplasmic space can be separated easily, by simple centrifugation of the yeast cells, from other proteins present in solution in the culture medium. Further, by treating the yeasts isolated from their culture medium with a minimum of a medium according to the invention, the protein of interest is released in a relatively concentrated form, while avoiding mixing with intracellular proteins.

The process of the invention can also be applied to the recovery of proteins secreted by yeasts immobilized by any means, including by fixation on a solid support or inside a polymer gel (e.g., an alginate or an acrylamide gel). Other applications which are obvious to those skilled in the art are within the scope of the present invention.

Similarly, although this invention is particularly appropriate for the recovery of heterologous proteins produced by yeasts of the *S. cerevisiae* species, as a result of a genetic manipulation, it can obviously be useful for the recovery of any polypeptide, whether heterologous or not, when it is localized in the yeast's periplasmic space. This is true regardless of the particular genus and species of the yeast.

The following Examples are illustrative of the claimed invention and should not be interpreted as limiting the scope thereof.

EXAMPLE 1

Yeast belonging to the species *Saccharomyces cerevisiae*, strain GRF 18 (auxotroph for leucine and histidine), and transformed by plasmid pLysΔ49 were grown at 28° C. in minimal medium (glucose: 3%; yeast nitrogen base; 0.67%) supplemented with 0.002% histidine. Plasmid pLysΔ49 comprises the gene LEU2 conferring prototrophy for leucine to the transformed yeast; it also contains the complete cDNA of chicken lysozyme (Belgian Patent No. 901,223; strain deposited at Centraal Bureau voor Schimmelcultures, Oosterstraat 1, Baarn, Netherlands on Dec. 5, 1984 under No. CBS 7130).

When the culture reached the stationary phase, an aliquot of 10 ml was centrifuged at 2,500 g for 10 minutes. The cells were then resuspended in 3 ml of 0.1M phosphate buffer with a pH of 6.5 supplemented with 0.5M NaCl and with a polyethoxylated p-octylphenol surfactant (product sold by Rohm & Haas under the trademark Triton X-100; the surfactant comprises generally 10 oxyethylene units per molecule) at a concentration of 0.05% by wt. By way of comparison, cells centrifuged from other aliquot parts of the culture were resuspended (1) in the phosphate buffer as such, (2) in the same buffer supplemented only with 0.5M NaCl, and (3) in a buffer supplemented only with 0.05% Triton X-100. After 60 minutes of incubation at 28° C. in the various media, the cells were separated again by centrifugation and lysozyme present in the supernatent was determined by the method of D. SHUGAR, supra. In order to determine the amount of lysozyme still associated with the cells, the latter were resuspended in the same media and ground by means of glass beads 5 minutes in a Braun homogenizer. After separation of the cellular debris by centrifugation at 12,500 g, the amount of lysozyme present in the supernatant was determined as above.

The results obtained are shown in Table 1. It is clear from the data that the addition of either 0.5M NaCl or of 0.05% Triton X-100 to the yeast suspension does not lead to any release of the lysozyme activity associated with the cells. This activity can only be detected in the homogenate obtained by grinding the cells in the presence of 0.5M NaCl. By grinding in the absence of NaCl or in the presence of Triton X-100, the measured activity reaches only 20 to 30% of the value observed in the presence of 0.5M NaCl. In contrast, a significant synergistic effect on the release of lysozyme from the cells is observed when both NaCl and Triton X-100 are present; in this case, 88% of the activity measured in the homogenate is found in the first supernatant.

The fact that the amount of lysozyme released by application of the process of the invention is close to the total amount of lysozyme detectable by grinding the cells demonstrates that the lysozyme is localized mainly in the yeast periplasmic space. However, it may happen in other cases that a non-negligible part of lysozyme not yet secreted into the periplasmic space is still intracellular. In such cases, the lysozyme yield recovered by the process of the invention should obviously be lower than that achieved in the present example.

TABLE 1

| Products added to 0.1M phosphate buffer with a pH of 6.5 | Lysozyme Activity* Released | | |
|---|---|---|---|
| | without grinding the cells (A) | by grinding (B) | total (A + B) |
| No product added | 0 | 5.3 | 5.3 |
| 0.5M NaCl | 0 | 25.6 | 25.6 |
| 0.05% Triton X-100 | 0 | 7.8 | 7.8 |
| 0.05% Triton X-100 + 0.5M NaCl | 22.6 | 1.8 | 24.4 |

*Lysozyme activity is expressed in units per ml of initial culture. The measured results were corrected for the effect of the surfactant and/or the salt on the activity of lysozyme.

EXAMPLE 2

The procedure described in Example 1 was repeated except that Triton X-100 was replaced by 1% Cemulsol OP-9 (polyethoxylated p-octylphenol having 9 oxyethylene units per molecule; product sold by Societe Francaise d'Organo Synthese). The results obtained are shown in Table 2.

It is clear from the data that 21% of the lysozyme produced by the yeast is released, without grinding, by 0.5M NaCl in the absence of a surfactant. This may be explained by adsorption on the yeast-wall of lysozyme already excreted into the medium. However, it should be noted that with the process of the invention, an amount of lysozyme four times higher is obtained in the medium. This again clearly shows the synergistic effect of both constituents when used together in the process of the invention.

TABLE 2

| Products added to 0.1M phosphate buffer with a pH of 6.5 | Lysozyme Activity Released | | |
|---|---|---|---|
| | without grinding the cells (A) | by grinding (B) | total (A + B) |
| No product added | 0 | 30.3 | 30.3 |
| 0.5M NaCl | 22.2 | 83.3 | 105.5 |
| 1% Cemulsol OP-9 | 26 | 30.3 | 56.3 |
| 1% Cemulsol PO-9 + 0.5M NaCl | 93.4 | 14.3 | 107.7 |

EXAMPLE 3

This Example illustrates the effect of the surfactant concentration on the release of lysozyme localized in the yeast periplasmic space, in accordance with the process of the invention.

The procedure of Example 1 was repeated, but after centrifugation the cells were resuspended in the 0.1M phosphate buffer with a pH of 6.5 supplemented with 0.5M NaCl and with various concentrations of Triton X-100. The results obtained after incubation of the cells, as described in Example 1, are shown in Table 3.

For concentrations of Triton X-100 of 0.01% and lower, no release of lysozyme was observed. On the contrary, at a concentration of 0.05% a significant release of the enzyme is observed which can still be improved by increasing the surfactant concentration beyond this value.

TABLE 3

| Products added to 0.1M phosphate buffer with a pH of 6.5 and 0.5M NaCl | Lysozyme activity released without grinding the cells |
|---|---|
| 0.001% Triton X-100 | 0 |
| 0.005% Triton X-100 | 0 |
| 0.01% Triton X-100 | 0 |
| 0.05% Triton X-100 | 24.4 |
| 0.1% Triton X-100 | 24.6 |
| 0.5% Triton X-100 | 29.6 |
| 1% Triton X-100 | 30.8 |

EXAMPLE 4

This Example illustrates the effect of the concentration of the soluble salt on the release of lysozyme localized in the yeast periplasmic space, in accordance with the process of the invention.

The procedure of Example 1 was repeated but after centrifugation the cells were resuspended in the 0.1M phosphate buffer with a pH of 6.5 supplemented with 0.05% Triton X-100, and with various concentrations of NaCl. The results obtained after incubation of the cells as in Example 1 are shown in Table 4.

For NaCl concentrations of 0.1M and lower, no release of lysozyme was observed. The lysozyme activity remained associated with the cells and could be partially measured by grinding. For NaCl concentrations of 0.25M and greater, lysozyme activity was detected in the supernatant and such activity reached a maximum for a concentration of 0.5M.

TABLE 4

| Product added to 0.1M phosphate buffer with a pH of 6.5 and 0.05% Triton X-100 | Lysozyme Activity Released | | |
|---|---|---|---|
| | without grinding the cells (A) | by grinding (B) | total (A + B) |
| 0.01M NaCl | 0 | 4.9 | 4.9 |
| 0.05M NaCl | 0 | 8.6 | 8.6 |
| 0.1M NaCl | 0 | 11.7 | 11.7 |
| 0.25M NaCl | 3.3 | 16.6 | 19.9 |
| 0.5M NaCl | 22.6 | 1.8 | 24.4 |
| 1M NaCl | 19.6 | 5.5 | 25.1 |

EXAMPLE 5

The procedure of Example 1 was repeated but with modified incubation times for the yeast cells in the phosphate buffer supplemented with 0.05% Triton X-100 and with 0.5M NaCl. The results obtained are shown in Table 5.

It is clear from the data that in order to release the lysozyme associated with the yeasts it is necessary to maintain contact between the cells and the medium for a sufficient period of time. After 30 minutes, a significant release of the lysozyme is observed, which can be further increased by increasing the incubation time.

TABLE 5

| | Lysozyme activity released by the salt and surfactant | | |
|---|---|---|---|
| Incubation time (min.) | without grinding the cells (A) | by grinding (B) | total (A + B) |
| 0 | 0 | 33.5 | 33.5 |
| 10 | 5.4 | 24.7 | 30.1 |
| 20 | 9.7 | 21.6 | 31.3 |
| 30 | 12.6 | 20.1 | 32.7 |
| 60 | 15.0 | 17.9 | 32.9 |

TABLE 5-continued

| | Lysozyme activity released by the salt and surfactant | | |
|---|---|---|---|
| Incubation time (min.) | without grinding the cells (A) | by grinding (B) | total (A + B) |
| 120 | 16.1 | 15.4 | 31.5 |

EXAMPLE 6

In this example, the effect of KCl is compared to that of NaCl. The procedure of Example 1 was repeated and the results obtained are shown in Table 6.

It is clear from the data that the addition of 0.5M KCl or NaCl to the yeast suspension medium does not lead to any release of the lysozyme activity associated with the cells. However, when the cells are suspended in a medium containing 0.5M KCl and 0.05% Triton X-100, lysozyme is released in the same proportions as those when NaCl is used as the soluble salt.

TABLE 6

| Products added to the 0.1M phosphate buffer with a pH of 6.5 | Lysozyme activity released without grinding the cells |
|---|---|
| 0.05% Triton X-100 | 0 |
| 0.5M NaCl | 0 |
| 0.5M KCl | 0 |
| 0.5M NaCl + 0.05% Triton X-100 | 45.9 |
| 0.5M KCl + 0.05% Triton X-100 | 43.3 |

EXAMPLE 7

This Example illustrates the influence of various surfactants conforming to the general formula in accordance with the invention. The difference between all these surfactants resides in the alkyl substitutes of the aromatic group Ar and in the number n of oxyethylene units. By way of comparison, other surfactants which do not correspond to the formula were tested.

The activity of these various surfactants was tested in the presence of 0.5M NaCl under the conditions described in Example 1. The results obtained are shown in Table 7. It is clear from the data that from all tested surfactants, only those whose hydrophobic part has an aromatic ring substituted in accordance with the invention are active.

TABLE 7

| Products* added to the 0.1M phosphate buffer with a pH of 6.5 and 0.5M NaCl | Lysozyme activity released without grinding the cells |
|---|---|
| 0.1% Polyoxyethylene ether W-1 (Sigman Chemical) | 0** |
| 1% Sorbitan monolaurate (Radiamuls 2125, Oleofina) | 0** |
| 1% Sorbitan monooleate (Span 80, Atlans Chem. Ind.) | 0** |
| 1% Polyethoxylated sorbitan monooleate (20) (Radiamuls 2137, Olefoine) (Tween 80, Atlas Chem. Ind.) | 0** |
| 1% Polyethoxylated sorbitan monostearate (20) (Radiamuls 2147, Oleofina) | 0** |
| 1% Polyethoxylated cetyl alcohol (20) (Brij 58, Atlas Chem. Ind.) | 0** |
| 0.2% Polyethoxylated p-octylphenol (9) (Cemulsol OP-9, SFOS) | 81 |
| 0.05% Polyethoxylated p-octylphenol (10) (Triton X-100 Rohm & Haas) | 88 |
| 0.2% Polyethoxylated p-nonylphenol (10) | 61 |
| (Synperonic NP 10, Imp. Chem. Ind.) | |
| 0.2% Polyethoxylated tributylphenol (8) (Sapogenat T-080, Hoechst) | 28 |

*Polyethoxylated compounds according to the invention have the number of oxyethylene units listed between the parenthesis.
**Comparative examples.

EXAMPLE 8

This Example illustrates the influence of surfactants whose general formula and HLB are in accordance with the present invention.

By way of comparison, other surfactants were tested. The latter surfactants fulfill the same general formula but their HLB's are outside the limits described in the present invention. The results obtained are shown in Table 8. It is clear from the data that in the latter case the release of lysozyme is weak or null.

TABLE 8

| Products* added to 0.1M phosphate buffer with a pH of 6.5 plus 0.5M NaCl (concentration: 0.2%) | Theoretical HLB | Lysozyme activity released by surfactant and NaCl without grinding of the cells |
|---|---|---|
| Polyethoxylated p-octylphenol (6) (Renex 756, Imp. Chem. Ind.) | 11.3 | 77 |
| Polyethoxylated p-octylphenol (9) (Cemulsol OP-9, SFOS) | 13.2 | 81 |
| Polyethoxylated p-octylphenol (14) (Symperonic OP 14, Imp. Chem. Ind.) | 15.0 | 16 |
| Polyethoxylated p-octylphenol (30) (Cemulsol OP 30, SFOS) | 17.3 | 0** |
| Polyethoxylated p-nonylphenol (8) (Lutensol AP 8, BASF) | 12.3 | 46 |
| Polyethoxylated p-nonylphenol (10) (Synperonic OP 10, Imp. Chem. Ind.) | 13.4 | 41 |
| Polyethoxylated p-nonylphenol (14) (Lutensol AP 14, BASF) | 14.8 | 4 |
| Polyethoxylated p-nonylphenol (23) (Arkopal N 230, Hoechst) | 16.4 | 0** |
| Polyethoxylated tributylphenol (4) (Sapogenat T-040, Hoechst) | 8.1 | 18 |
| Polyethoxylated tributylphenol (8) (Sapogenat T-080, Hoechst) | 11.4 | 32 |
| Polyethoxylated tributylphenol (18) (Sapogenat T-180, Hoechst) | 15.0 | 0** |
| Polyethoxylated tributylphenol (30) (Sapogenat T-300, Hoechst) | 16.7 | 0** |

*The number of oxyethylene units per molecule is listed between parenthesis.
**Comparative examples.

What is claimed is:

1. A process for releasing into an aqueous medium polypeptides produced by yeasts belonging to the Saccharomyces genus and localized at least partially in the periplasmic space thereof, comprising treating an aqueous medium of yeasts capable of producing polypeptides, without breaking said yeasts, with a neutral water-soluble mineral salt selected from the group consisting of NaCl, KCl, $NaNO_3$, $KNO_3$, and $Na_2SO_4$ used at a concentration in the medium of at least 0.1M and a nonionic water-soluble polyethoxylated alkylphenol surfactant having an HLB from about 8 to about 15, wherein said polypeptides are released into said aqueous medium.

2. The process according to claim 1, wherein the yeasts have been genetically manipulated to produce a polypeptide.

3. The process according to claim 1, wherein the yeasts have been genetically manipulated to produce a heterologous polypeptide.

4. The process according to claim 3, wherein the heterologous polypeptide is a lysozyme.

5. The process according to claim 1, wherein the yeasts belong to the species *Saccharomyces cerevisiae*.

6. The process according to claim 5, wherein the yeasts belong to the strain GRF 18.

7. The process according to claim 1, wherein the non-ionic surfactant is used at a concentration of at least 0.02%.

8. The process according to claim 1, wherein the non-ionic surfactant is selected from the group consisting of polyethoxylated octyl- and nonylphenols having an HLB of between 10 and 15.

9. A process for releasing into an aqueous medium polypeptides produced by yeasts belonging to the Saccharomyces genus and localized at least partially in the periplasmic space thereof, comprising treating an aqueous medium of yeasts capable of producing polypeptides, without breaking said yeasts, with NaCl, KCl, $NaNO_3$, $KNO_3$, or $Na_2SO_4$ used at a concentration in the medium of at least 0.1M and a non-ionic water-soluble polyethoxylated tributyl phenol surfactant having an HLB of between 8 and 12.5.

* * * * *